(12) United States Patent
Enoch

(10) Patent No.: US 7,730,890 B2
(45) Date of Patent: Jun. 8, 2010

(54) SNORE RELIEF WITH MANDIBULAR POSITIONING DEVICE

(76) Inventor: Harold Enoch, 2155 Post Oak Tritt Rd., Suite 180, Marietta, GA (US) 30062

( * ) Notice: Subject to any disclaimer, the term of this patent is extended or adjusted under 35 U.S.C. 154(b) by 42 days.

(21) Appl. No.: 11/515,624

(22) Filed: Sep. 5, 2006

(65) Prior Publication Data

US 2008/0053463 A1    Mar. 6, 2008

(51) Int. Cl.
A61F 5/56    (2006.01)
A61C 5/14    (2006.01)
A61C 3/00    (2006.01)

(52) U.S. Cl. ............................. 128/848; 128/861; 433/6
(58) Field of Classification Search ......... 128/859–863, 128/846; 433/6, 34, 36, 37; 602/902
See application file for complete search history.

(56) References Cited

U.S. PATENT DOCUMENTS

| 4,901,737 | A |  | 2/1990 | Toone |  |
| 5,092,346 | A | * | 3/1992 | Hays et al. | 128/848 |
| 5,316,020 | A | * | 5/1994 | Truffer | 128/848 |
| 5,566,683 | A |  | 10/1996 | Thornton |  |
| 5,915,385 | A | * | 6/1999 | Hakimi | 128/848 |
| 5,941,247 | A |  | 8/1999 | Keane |  |
| 6,494,209 | B2 |  | 12/2002 | Kulick |  |
| 6,516,805 | B1 |  | 2/2003 | Thornton |  |
| 6,619,290 | B1 |  | 9/2003 | Zacco |  |
| 6,729,335 | B1 |  | 5/2004 | Halstrom |  |
| 2003/0121520 | A1 |  | 7/2003 | Parker |  |
| 2007/0079833 | A1 | * | 4/2007 | Lamberg | 128/848 |

* cited by examiner

Primary Examiner—Patricia M Bianco
Assistant Examiner—Tarla R Patel
(74) Attorney, Agent, or Firm—Woodcock Washburn LLP

(57) ABSTRACT

A one piece mouthpiece with a mandibular re-positioning extension for reducing snoring, and in particular, to a dental orthosis for easy engagement with the upper dentition of a person and intended to eliminate snoring. The mouthpiece is made from a deformable material with a shape complementary to a person's upper teeth and dental arch. The mouthpiece generally has an arched channel which embraces the upper teeth of a person. The mouthpiece includes an attached downward anterior mandibular extension located at the back of the top of the arch of the mouthpiece.

16 Claims, 4 Drawing Sheets

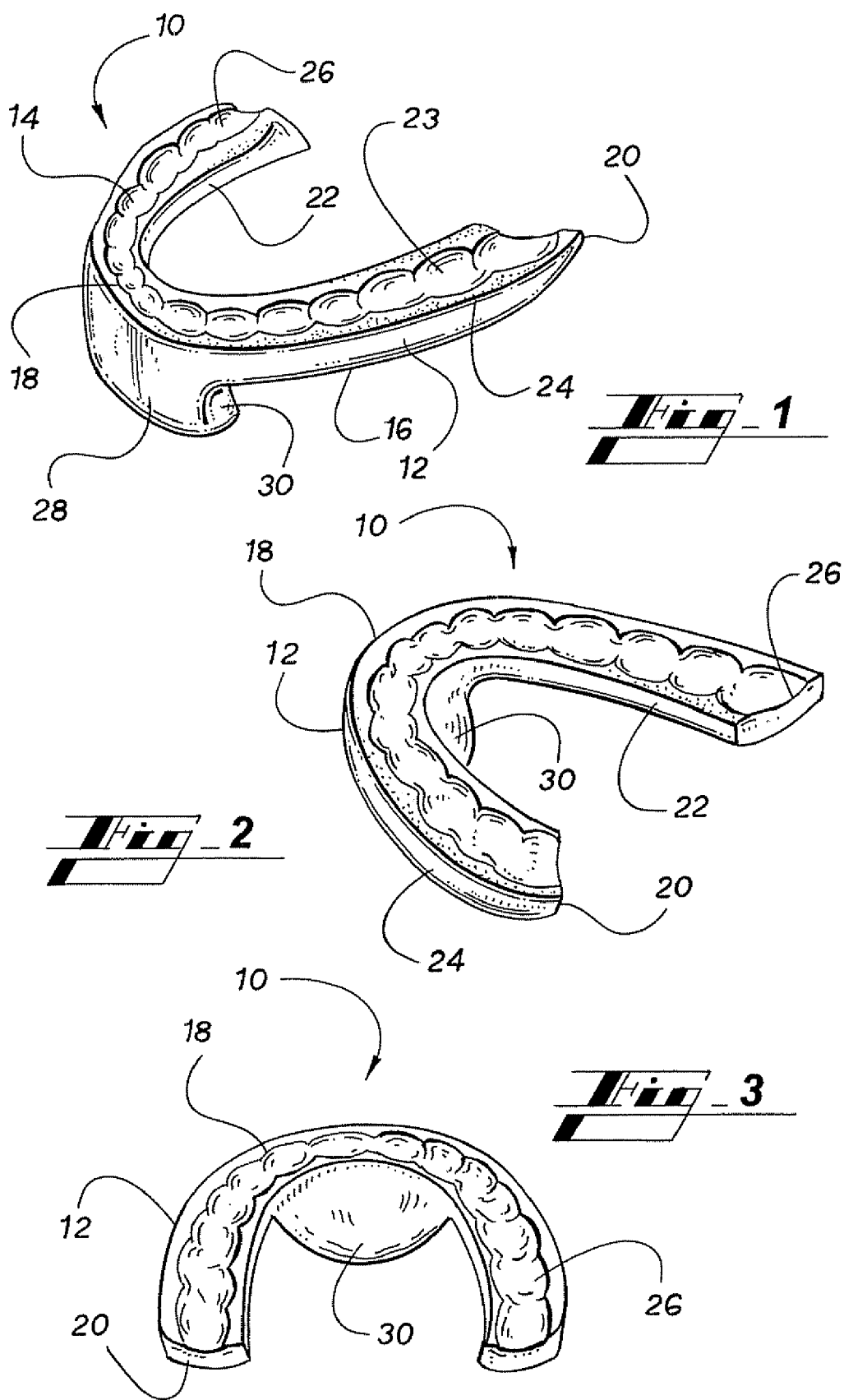

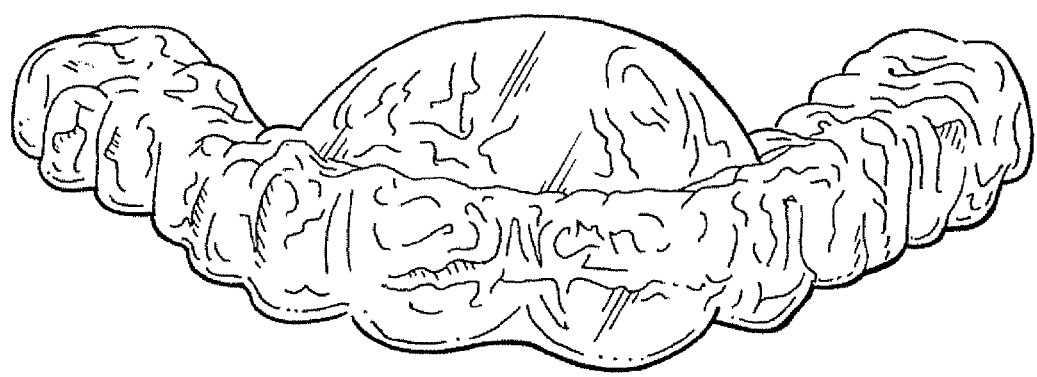
FIG_4
FIG_5
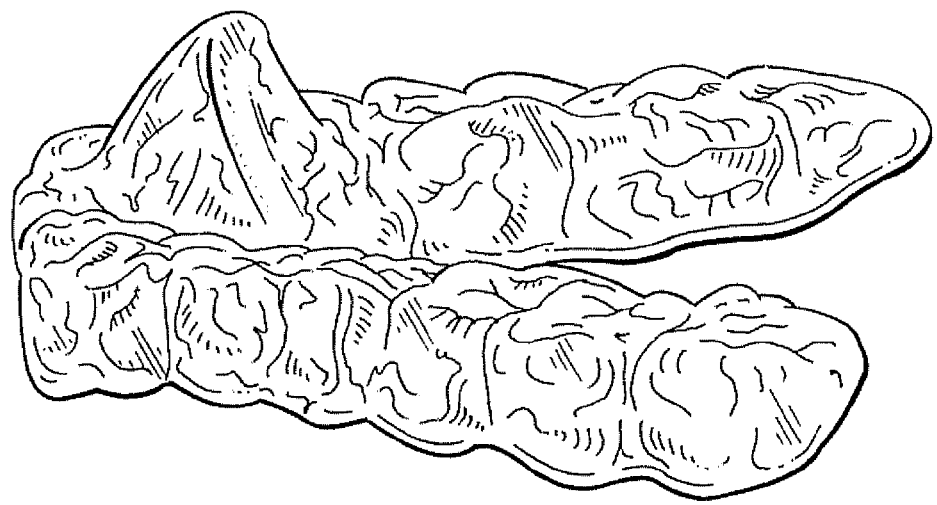

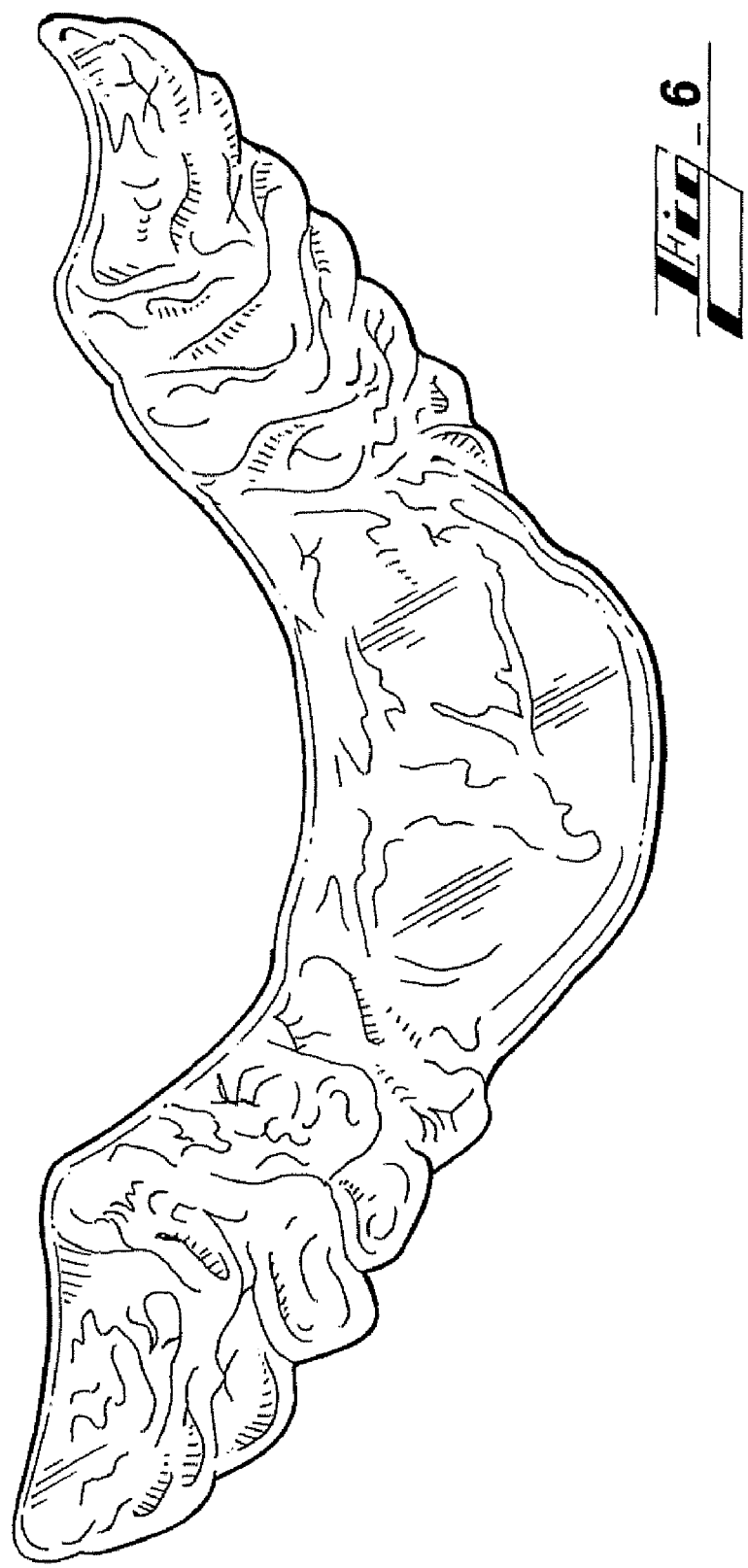
Fig_6

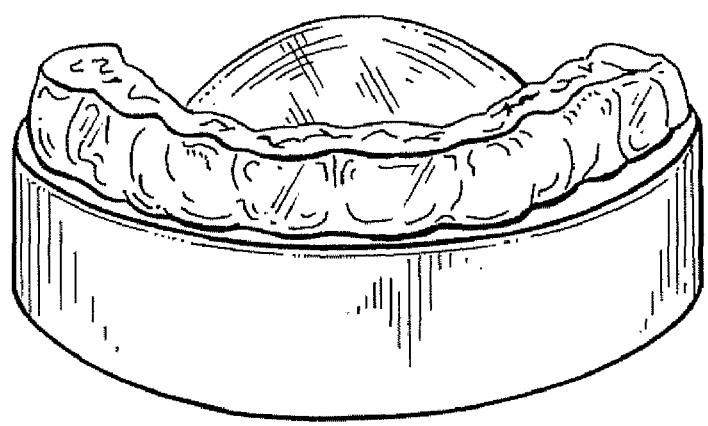
Fig_7
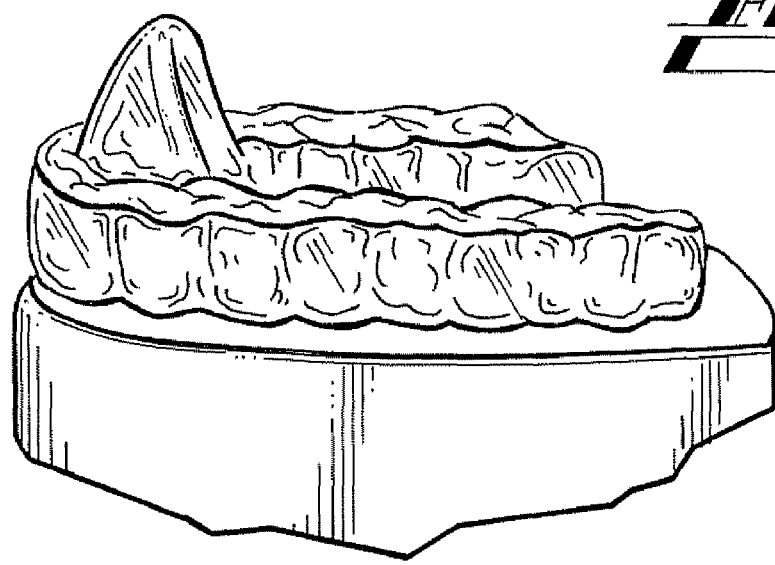
Fig_8

SNORE RELIEF WITH MANDIBULAR POSITIONING DEVICE

TECHNICAL FIELD

The present disclosure relates generally to an oral apparatus for reducing snoring, and more specifically, to a dental mouthpiece for easy engagement with the teeth of a user to reduce snoring.

BACKGROUND ART

Snoring is typically caused by partial obstruction of an individual's airway during sleep. Snoring occurs when the pharyngeal airway is partially obstructed, resulting in vibration of the oral tissues during respiration. Snoring tends to become more severe as patients grow older, likely due to progressive loss of muscle tone in the patient's throat and oral tissues.

In these respects, the snore relieving apparatus with mandibular positioning according to the present disclosure substantially departs from the conventional concepts and designs of the prior art, and in so doing provides an apparatus primarily developed for the purpose of reducing snoring, and in particular, to a mouthpiece for easy placement on the upper teeth of a user, comfortable to wear, and which permits the natural movement and positioning of the lower jaw. In addition, the mandibular positioning piece is small enough so as to not position the tongue in an irritating and uncomfortable position.

SUMMARY OF THE DISCLOSURE

The general purpose of the present disclosure, which will be described subsequently in greater detail, is to provide a mouthpiece with an oral anterior mandibular positioning piece that is primarily developed for the purpose of reducing snoring, and in particular, this one-piece snoring mouthpiece fits on the upper teeth and arch of the mouth to help prevent snoring by positioning the lower jaw forward.

To attain this, the present disclosure generally comprises an arched channel made up of a deformable material adapted to be engaged with the upper teeth of a user. The upper member may further comprises front and rear ends, and upper and lower surface portions. The mouthpiece further comprises inner and outer upstanding wall portions extending upwardly from upper surface portion to define a channel for receiving at least a portion of some of the teeth of the upper dentition in user's mouth. Further, a mandibular downward positioning piece extends from the anterior of the arched channel to press against the tongue so as position the lower jaw forward and reduce snoring.

In another embodiment, the anterior mandibular extension may suspend downwardly from front end of the arched member. The anterior mandibular extension may further comprise an interior surface and an exterior surface. The interior surface of anterior mandibular extension is a shaped piece and is used to maintain the user's tongue in a forward position thereby positioning the lower jaw forward.

In addition, it may be noted that the described mouth piece, including the anterior mandibular extension, may be flavored and made of colored or non-colored materials.

To accommodate the mouth of the user, each mouth piece is custom made to fit the upper dentition; using a mold made from the upper dentition and a warm deformable material vacuum sucked over the custom mold. The size of the anterior mandibular extension and teeth channel may be modified to fit the mouth and arch of each user.

BRIEF DESCRIPTION OF DRAWINGS

Some of the features, advantages and benefits of the present mouthpiece having been stated, others will become apparent as the description proceeds when taken in conjunction with the accompanying drawings, presented solely for exemplary purposes and not with the intent to limit the disclosure thereto, and in which:

FIG. 1 illustrates a top view from the front side of the oral apparatus for reducing snoring in accordance with one embodiment of the present disclosure.

FIG. 2 illustrates a top view from the rear side of the oral apparatus for reducing snoring in accordance with one embodiment of the present disclosure.

FIG. 3 illustrates a rear elevation view of the oral apparatus for reducing snoring in accordance with one embodiment of the present disclosure.

FIG. 4 illustrates a front bottom perspective view of the oral apparatus for reducing snoring in accordance with one embodiment of the present disclosure.

FIG. 5 illustrates a bottom right perspective view of the oral apparatus for reducing snoring in accordance with one embodiment of the present disclosure.

FIG. 6 illustrates a bottom rear perspective view of the oral apparatus for reducing snoring in accordance with one embodiment of the present disclosure.

FIG. 7 illustrates a front top view of the oral apparatus for reducing snoring in accordance with one embodiment of the present disclosure situated over an upper arch of user's mouth.

FIG. 8 illustrates a bottom right perspective view of the oral apparatus for reducing snoring in accordance with one embodiment of the present disclosure situated over an upper arch of user's mouth.

DESCRIPTION OF SPECIFIC EMBODIMENTS

The present disclosure will now be described more fully hereinafter with reference to the accompanying drawings, in which preferred embodiments of the disclosure are shown. This disclosure, may, however be embodied in many different forms and should not be construed as limited to the illustrated embodiments set forth herein. Rather, these illustrated embodiments are provided so that this disclosure will be thorough and complete, and will fully convey the scope of the disclosure to those skilled in the art.

FIGS. 1-8 illustrate various aspects of the mouthpiece herein described. The mouthpiece, in one embodiment, may be illustrated in FIGS. 1-8. FIGS. 1-3 illustrate a one-piece anti-snoring device 10 according to the teachings of the present disclosure. As shown in FIG. 1, the mouthpiece body as seen in 10 comprises a u-shaped upper arch 12 configured as a channel 26 embracing some of the upper teeth of a user (not shown). The mouthpiece body as seen in 10 comprises a u-shaped upper arch 12 configured as a channel 26, the upper arch and channel can be u-shaped, c-shaped, oval shaped or the general shape of a person's upper dentition. A channel 26 may be defined between inner and outer wall portions 22, 24 and may be generally custom created to fit the teeth of the upper dentition. The channel may embrace all of the upper dentition or a few of the upper teeth. Depending upon the size of the mouth of the user, the distance between inner and outer wall portions 22, 24 may be varied, further the size and thickness of the anterior mandibular extension 28 and 30 will also vary so as to keep the teeth in harmony with the jaw when the mouthpiece is inserted.

As illustrated in FIGS. 1-8, the entire apparatus 10 may be formed from a deformable material for use in a person's mouth, while maintaining its over-all shape of the upper dentition of a person.

The mouthpiece body 12 may be provided with front 18 and back 20 ends and upper 14 and lower 16 surfaces consistent to a person's upper dental arch configured to embrace the upper teeth of a person. The mouthpiece body 12 also includes a mandibular anterior extension 28 and 30 suspended downward and out from the mouthpiece 10 and aligned against the back of the front teeth of a person's mouth. The anterior mandibular extension 28 and 30 can be oval, square, round, triangle, rectangular or shaped as a whale tail.

Upper arch 12 also includes front and rear ends 18 and 20, respectively, and an downward anterior mandibular extension 28 and 30 attached to upper arch 12 at front end 18. Inner and outer wall portions 22 and 24 respectively, extend upwardly from inner and outer edges of upper surface portion 14. Inner and outer wall portions 22, 24 extend rearward from front end 18 of upper arch 12 towards the rear of a user's upper teeth.

In one embodiment of FIGS. 1-3, the upper arch 12 is constructed of a deformable material. To construct the mouthpiece 10, the person's upper teeth are impressed into a wax bite and such wax bite impression is used as a mold for the creation of the mouthpiece. The mouthpiece 10 is made from a deformable material poured over the wax bite mold and vacuum sucked to the mold. The mouthpiece includes a custom groove 23, created from the impression of the person's upper teeth so that it is capable of being comfortably attached to the person's upper teeth when properly placed within the mouth.

As further illustrated in FIG. 3, the mouthpiece body 12 includes a mandibular anterior extension 28 attached at front end 18 and shaped for a comfortable, temporary contact with the tongue. The mandibular anterior extension 30 which contacts the tongue may be shaped so as to allow for more comfortable extension of the lower jaw.

In FIGS. 1-3 may also be coated with a flavored substance or colored material. The downwardly extending mandibular anterior extension 28 comprises an interior surface 30 and an exterior surface 32. During the custom fitting of the mouthpiece 10, as more fully addressed below, the mandibular anterior extension 30 and 28 may be constructed so as to conform to the upper bridge of a person's mouth while maintaining the natural alignment of the jaw. Based on examination of user's jaw, mouth and teeth by a dentist, downwardly extending mandibular anterior extension 28 and 30 may be also custom configured to be of a thickness and length, such that when mouthpiece 10 may be comfortably inserted and fitted over the upper teeth, with the downward mandibular anterior extension 30 engaging the user's tongue so as to push the lower jaw forward, and increase air flow thereby eliminate snoring. It may be noted that the mandibular anterior extension 28 and 30 may be uniformly molded with the mouthpiece body 12 in accordance with one embodiment of the disclosure.

The mandibular anterior extension 28 may contain an interior surface 30 which may be textured or smooth. When the mouth piece 10 is fitted onto the person's upper teeth, the interior surface 30 of mandibular anterior extension pushes a person's tongue forward, by contacting the tongue and interior surface 30 of mandibular anterior extension 28. As an additional benefit, the alignment of the mandibular anterior extension against the back of the front teeth causes a user's tongue to be pushed back and jaw of said user to be advanced forward, increasing airflow and thereby reducing snoring.

In one embodiment, the downwardly extending mandibular anterior extension piece 28 and 30 extends downward and serves to shift the user's lower jaw forward, the size, shape and thickness of the mandibular anterior extension 28 and 30 may be determined by the anatomy of the user's lower dentition and jaw structure, as well as the user's natural jaw alignment. The size and thickness of the mandibular anterior extension will depend on the size and shape of a person's mouth so as to keep the mandible in the most forward position while keeping in harmony with the jaw, or the jaws natural resting position.

Mouthpiece 10 should be created and fitted by a dentist to ensure proper fitting and placement of the mandibular anterior extension. The downwardly mandibular anterior extension 28 may be then configured with the appropriate thickness and proper length and angling to provide the optimal forward shift of the lower jaw outward.

Mouthpiece 10 may also be created using pre-made large or small molds which may then be fitted to the person's upper teeth and custom sized for optimum fit, as illustrated in FIGS. 4-8. The pre-made molds are softened by placing them in hot water or other chemical material causing the mold to soften. The softened pre-made mold 10 is placed in a user's mouth. Additional deformable resin may be filled within channel or groove 26 so that the resin forms an impression of the person's upper teeth so as to provide for a custom fit. After the deformable material and groove 26 sets and hardens, the dentist adjusts the mouthpiece 10 to further conform to the person's mouth trimming and conforming the portions of mouthpiece 10 which do not match the mold of the person's mouth or are uncomfortable to the user.

FIGS. 4-8 illustrates the embodiment apparatus in situ. As shown, the teeth of the upper dentition are positioned within channel of upper arch. When the user's mouth closes naturally, as when asleep, downwardly extending mandibular anterior extension presses against the back of the front teeth and engages the tongue, thereby pushing the lower jaw forward. Furthermore, the mouthpiece by moving the lower jaw forward while a person lays down, opens the airway of said person allowing for the easy inhalation and exhalation of air.

The one-piece device allows for forward location of the user's lower jaw which is caused by the whale-tale or tongue-like shaping of the downward mandibular anterior extension from the upper arch. This shape allows for an effective and comfortable snoring dental apparatus.

The mouthpiece seen in FIGS. 4-8, when worn properly on the upper dentition, allows for the mandibular anterior extension to press the tongue back, shift the lower jaw forward, so as to be in harmony with the jaw, enlarging the airway of the user between the tongue and uvula and the movable fold, consisting of muscular fibers enclosed in a mucous membrane, that is suspended from the rear of the hard palate and closes off the nasal cavity from the oral cavity during swallowing or sucking, e.g. soft palate. The enlargement of the breathing airway works to reduces the vibrations of the soft palate and uvula thereby reducing snoring.

While the disclosure has been described in connection with the specific embodiments thereof, it will be understood that it may be capable of further modification. Furthermore, this application may be intended to cover any variations, uses, or adaptations of the disclosure, including such departures from the present disclosure as come within known or customary practice in the art to which the disclosure pertains.

What is claimed is:

1. A mouthpiece for use by a person during sleep to reduce snoring, said mouthpiece comprising:
   a mouthpiece body customized to orient the person's lower jaw in a position of neutral alignment with respect to the person's natural bite, whereby the lower jaw is restrained from posterior movement while said mouthpiece body is being worn; and
   a mandibular anterior extension suspended downward and out from said mouthpiece, said mandibular anterior extension aligned against a back of a front tooth of the person's mouth, wherein alignment of the mandibular anterior extension against the back of the front tooth causes the person's tongue to be pushed back and his jaw to be placed in a position of natural alignment with respect to the jaw and tooth, thereby moving the person's soft palate into a position whereby his airway is opened to increase air flow and reduce snoring.

2. The mouthpiece of claim 1, wherein said mouthpiece further comprises upper and lower surfaces and front and back portions.

3. The mouthpiece of claim 2, wherein said mouthpiece further comprises an arched channel comprising an inner and outer upstanding wall for embracing upper teeth of the person's mouth.

4. The mouthpiece of claim 3, wherein said mouthpiece has said anterior mandibular extension extending downward from a top of said arch on said inner wall of said channel.

5. The mouthpiece of claim 1, wherein said body comprises a deformable material, and wherein said deformable material is flavored.

6. The mouthpiece of claim 1, wherein said body comprises a deformable material, and wherein said deformable material is colored.

7. The mouthpiece of claim 1, wherein said body comprises a deformable material, and wherein said deformable material is textured.

8. The mouthpiece of claim 1, wherein said body comprises a deformable material, and wherein said deformable material is smooth.

9. A one-piece mouthpiece for use by a person during sleep to reduce snoring, said mouthpiece comprising:
   a mouthpiece body having front and back ends, and upper and lower surfaces consistent to an upper dental arch of the person and adapted to embrace upper teeth of the person; and
   said mouthpiece body comprising a deformable material and customized to orient the person's lower jaw in a position of neutral alignment with respect to the person's natural bite, whereby the lower jaw is restrained from posterior movement while said mouthpiece body is being worn, said mouthpiece body further having an attached anterior mandibular extension positioned downward so that, when worn, said mandibular anterior extension is located in back of front teeth of the person and acts to position the tongue back into the mouth of the person and to move a jaw of the person to its position of natural alignment.

10. The mouthpiece of claim 9, wherein said mouthpiece is formed according to a size of the person's mouth, dental arch and jaw.

11. A method for reducing snoring during sleep, the method comprising the steps of:
   creating a mouthpiece customized to orient a person's lower jaw in a position of neutral alignment with respect to the person's natural bite, whereby the lower jaw is restrained from posterior movement while said mouthpiece body is being worn, said mouthpiece based on a wax bite impression of the person's upper dentition, wherein the mouthpiece is made from a deformable material, said deformable material vacuum drawn over the wax bite impression of the person's upper dentition; and
   inserting the mouthpiece over upper teeth of the person, the mouthpiece having front and back ends, and lower and upper surfaces having a shape consistent with a upper dental arch of the person, and having an anterior downwardly-positioned mandibular anterior extension portion attached inside the top of the arch of the mouthpiece and positioned behind front teeth of the person,
   wherein the mandibular anterior extension portion is operable to reposition a tongue of the person and move a jaw of the person to a position of natural alignment, allowing for free flow of air and reduction in snoring.

12. A device for alleviating snoring comprising:
   a body adapted to engage at least a portion of a wearer's upper dentition, said body having a depending anterior extension,
   said body customized to orient the wearer's lower jaw in a position of neutral alignment with respect to the wearer's natural bite, whereby the lower jaw is restrained from posterior movement while said mouthpiece body is being worn,
   wherein said depending anterior extension is adapted to abut a surface of at least a portion of a lower dentition of the wearer to maintain a jaw of the wearer in a position of natural alignment to prevent obstruction of an airway of the wearer.

13. The device of claim 12, wherein said anterior extension is adapted to allow natural movement of the wearer's jaw.

14. The device of claim 12, further comprising a custom groove formed in an upper surface of said body.

15. The device of claim 12, wherein said body is adapted to embrace a plurality of upper teeth of the wearer's upper dentition.

16. The device of claim 12, wherein at least on of a size, a shape, and a thickness of said anterior extension is determined by a natural jaw alignment of the wearer's jaw.

* * * * *